United States Patent [19]

Segura

[11] 4,116,416
[45] Sep. 26, 1978

[54] DENTAL MOLD

[76] Inventor: Claude Ginés Fernand Segura, Ave. des Pervenches, Perpignan, France, 66000

[21] Appl. No.: 729,950

[22] Filed: Oct. 6, 1976

[30] Foreign Application Priority Data

Oct. 6, 1975 [FR] France ............................ 75 31208

[51] Int. Cl.² .................... A61C 13/12; B29C 1/16
[52] U.S. Cl. .................................... 249/54; 32/11; 32/71; 425/179
[58] Field of Search ................ 32/11, 32, 17, 71; 249/54, 66 A, 66 C, 69, 70, 121; 425/179, 180

[56] References Cited

U.S. PATENT DOCUMENTS

| 2,312,171 | 2/1943 | Jochum | 32/17 |
| 2,700,219 | 1/1955 | Lindley | 32/32 |
| 2,712,158 | 7/1955 | Villa | 425/180 |
| 2,980,248 | 4/1961 | Embring | 249/121 |
| 3,650,032 | 3/1972 | Kestler | 32/11 |
| 3,702,027 | 11/1972 | Marshall | 32/11 |
| 3,808,689 | 5/1974 | Spinella | 32/32 |
| 4,022,419 | 5/1977 | Haker | 249/54 |

Primary Examiner—Francis S. Husar
Assistant Examiner—John S. Brown
Attorney, Agent, or Firm—Karl F. Ross

[57] ABSTRACT

A mold for the temporary retention of two or more false dental roots in a mass of plaster of paris or the like has a shell with a curved trough, of an outline conforming to that of all or part of the human jaw, which is of upwardly diverging trapezoidal cross-section and whose side and bottom surfaces are transversely corrugated for precisely locating any one-root segment of the molded mass temporarily removed from the mold. The trough is partly overlain by a retractable slider whose removal facilitates extraction of the mass. The bottom of the mold has a pair of longitudinally tapering, dovetail-shaped rails of a nonadhering material by which it is removably fitted into the plaster-of-paris layer of an articulator.

9 Claims, 7 Drawing Figures

DENTAL MOLD

FIELD OF THE INVENTION

My present invention relates to a mold for the temporary retention of two or more so-called false dental roots in a relative position determined by a patients's jaw, preparatorily to the building of a partial or total denture around these roots.

BACKGROUND OF THE INVENTION

In making such multitooth dentures it is known to use a mold in which the false roots are disposed, in positions determined by an impression taken from the patient's mouth, within a hardenable cementitious mass generally consisting of plaster of paris. The mold is fastened with the aid of a similar mass to an articulator so as properly to confront a replica of the opposite jaw. After suitable alignment of the mold and the false roots, the latter are usually extracted from the mold together with the surrounding cementitious body which is thereafter cut apart between the roots to allow the fitting of a false tooth to each of them. It is then necessary to reinsert the root and its surrounding cementitious segment into the mold in exactly the position previously occupied by it. Owing to the removal of some of the cementitious material by the saw cut, however, there is now always a gap between adjoining segments so that precise repositioning is difficult.

Moreover, the mold can rarely be removed from the articulator without destroying its seat in the cementitious layer so that accurate reinsertion into that layer creates a problem.

OBJECTS OF THE INVENTION

An important object of my present invention, therefore, is to provide an improved dental mold for the purpose set forth which avoids the aforestated drawbacks and which, in particular, facilitates the accurate repositioning therein of segments cut from a body of plaster of paris or other cementitious material encasing a plurality of false roots.

Another object is to provide means on such a mold for anchoring it to a relatively fragile cementitious layer in a manner enabling its repeated removal and reinsertion in the same position.

A further object is to provide simple and reliable means for releasably retaining the cementitious body with its array of false roots in such a mold.

SUMMARY OF THE INVENTION

In accordance with my present invention, a mold of the character described comprises a shell with an upwardly open trough whose outline conforms to all or part of a human jaw and which has a generally trapezoidal, upwardly diverging cross-section whose bottom and side surfaces are provided with closely spaced transverse corrugations to facilitate the precise repositioning of a segment of a molded mass in that trough after temporary removal therefrom.

According to another feature of my invention, the mold is provided on its underside with one or more dovetail-shaped rails which are receivable in a layer or hardenable cementitious material on an articulator, these rails preferably converging toward one end thereof to insure that their withdrawal from the layer leaves the latter intact and to define exactly the relative position of the mold and the articulator.

Pursuant to a further feature of my invention, a slider removably seated in the mold shell has a shelf partly overhanging the trough for holding the cementitious mass in place while giving access to it from above, thereby enabling the introduction of the false roots into the trough and their suitable positioning within the still fluid mass in the working position of the slider.

BRIEF DESCRIPTION OF THE DRAWING

The above and other features of my invention will now be described in detail with reference to the accompanying drawing in which.

SPECIFIC DESCRIPTION

Figure 1:
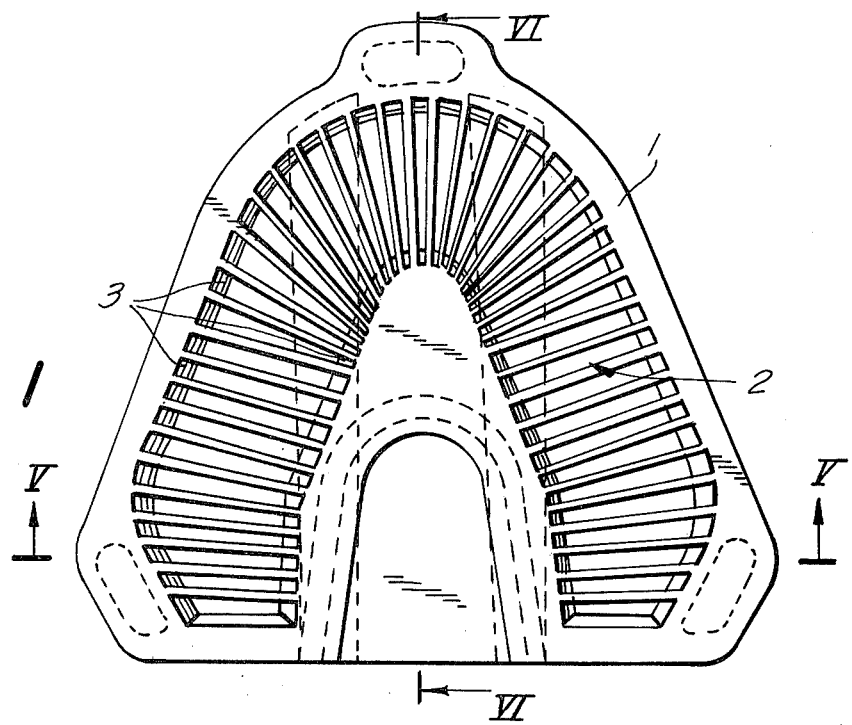
FIG. 1 is a top view of a mold, according to my invention, for a total denture.

As shown in FIGS. 1 – 6, a dental mold according to my invention comprises a rigid shell 1 formed with an upwardly open, generally U-shaped trough 2 of substantially trapezoidal cross-section, with the major base of the trapezoid lying on top. The shell 1 may consist of metal or hard plastic (the letter being indicated in the drawing). Trough 2 is defined by an outer sidewall 1a, an inner sidewall 1b and a bottom 1c of shell 1.

In accordance with an important feature of my invention, the side and bottom surfaces of the trough 2 are provided with closely spaced transverse corrugations 3 which lie in vertical planes so as to facilitate the upward withdrawal of a nonillustrated molded mass from the trough. That molded mass, usually consisting of plaster of paris, has embedded therein a multiplicity of false roots at locations corresponding to the positions of the teeth of the opposite jaw of a patient as determined by an impression taken from the patient's mouth. The spacing of the corrugations 3 should be substantially smaller than that of the roots in order that a segment of the molded cementitious body, containing one such root, should have several ribs on each of three sides whereby the exact location of the segment within that trough is unequivocally established.

Figure 5:
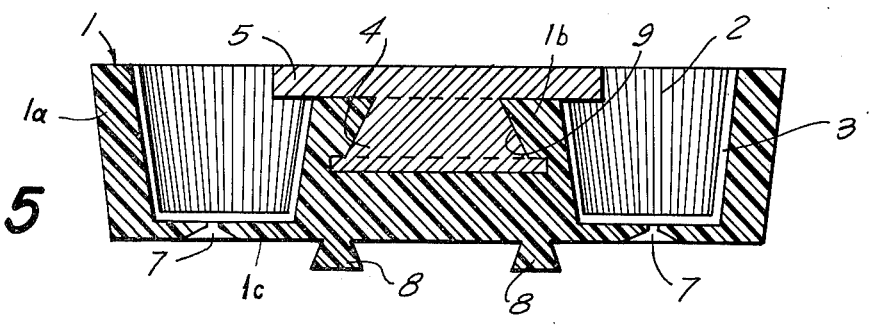
FIG. 5 is a cross-sectional view taken on the line V — V of FIG. 1; with the slider in place.
Figure 6:
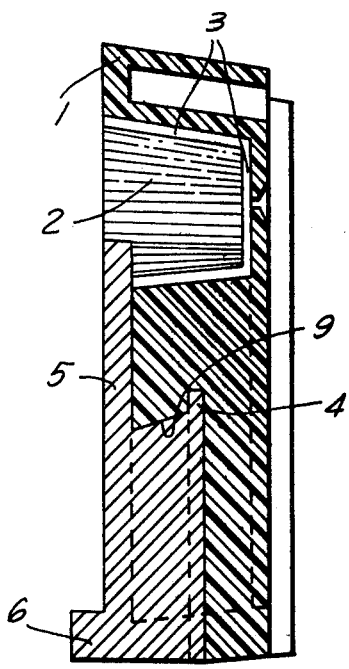
FIG. 6 is a cross-sectional view taken on the line VI — VI of FIG. 1, also with the slider in place.
Figure 3:
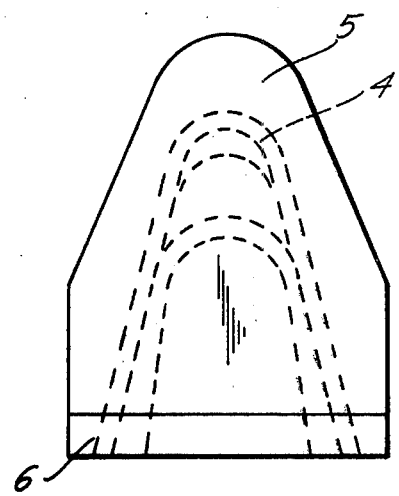
FIG. 3 is a top view of a slider (omitted in FIG. 1) receivable in the mold.
Figure 4:
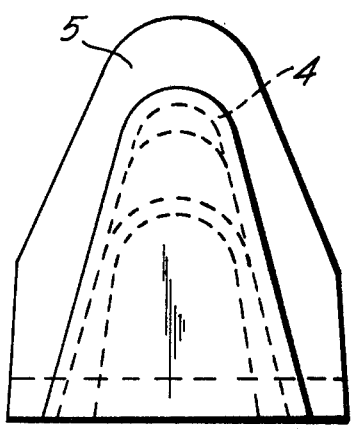
FIG. 4 is a bottom view of the slider shown in FIG. 3.

As shown in FIGS. 5 and 6, a central portion of shell 1 forming the inner sidewall 1b has a dovetail-shaped groove 9 complementary to that of a key 4 forming part of a slider of generally T-shaped profile, the key constituting the web of the "T" whose bar forms a shelf 5 overhanging the trough 2 which is thereby partly obstructed from above. As best seen in FIGS. 3 and 4, the shelf 5 of the slider is generally tongue-shaped and has a contour following the outline of the trough 2, the tip of the tongue pointing toward the bight of the "U". Slider 4, 5 also has an upstanding cleat 6 enabling its manual withdrawal from the groove 9 in the direction away from that bight, i.e. downwardly as viewed in FIGS. 1 and 6. The top of shell 5 is flush with the rim of shell 1 so as not to interfere with the closure of a simulated pair of jaws (one of them represented by the mold) on a nonillustrated articulator to which the mold is fastened through the intermediary of a layer of plaster of paris or the like.

Figure 2:
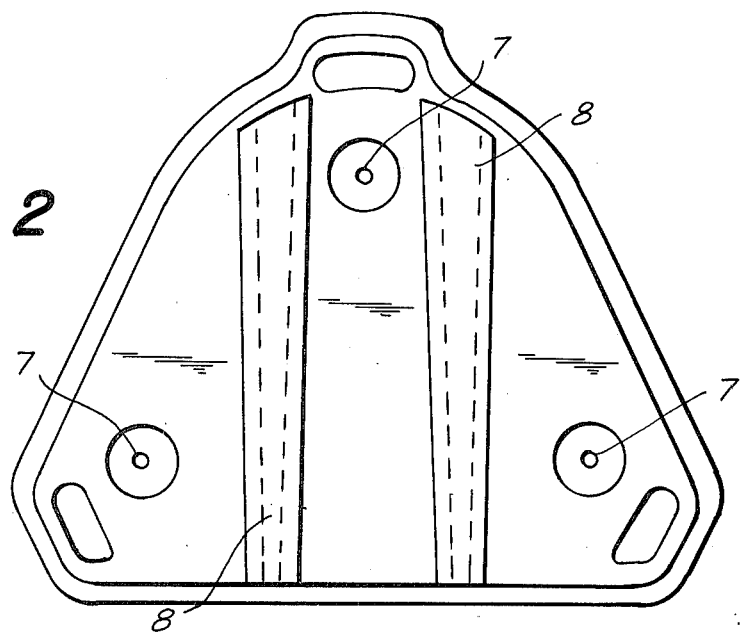
FIG. 2 is a bottom view of the mold shown in FIG. 1.

In order to anchor the mold to that layer, the underside of shell 1 is formed with a pair of parallel rails 8 of a dovetail-shaped profile converging longitudinally toward one end thereof as best seen in FIG. 2. These rails 8 permit the nondestructive removal of the mold from the relatively fragile layer, especially if they consist of or are coated with a substance which is nonadhering to the material of that layer (i.e. plaster of paris). Suitable substances of this nature includes polyethylene and polytetrafluoroethylene (Teflon).

The bottom of shell 1 is advantageously perforated with small orifices 7 through which air under pressure may be introduced into the trough 2 for aiding in dislodging the molded mass with its embedded false roots after withdrawal of the slider 4, 5.

Figure 7:
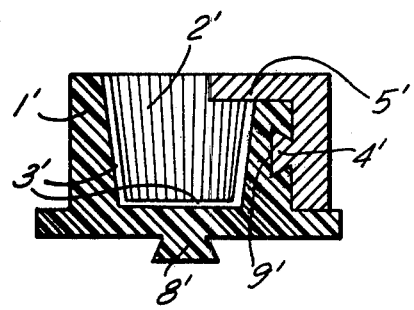
FIG. 7 is a cross-sectional view generally similar to FIG. 5, relating to a modified mold designed for a partial denture.

Whereas the mold shown in FIGS. 1 – 6 is designed to hold the roots of a full complement of false teeth, my invention is also applicable to smaller molds used in making partial dentures. Such a smaller mold has been illustrated in FIG. 7 where a shell 1' has a trough 2' of limited dimensions designed to receive two or more false roots, the side and bottom surfaces of this trough having transverse corrugations 3' as described above. The bottom of the mold carries a single dovetail-shaped rail 8' and one of the trough walls is formed with an external keyway 9' receiving a dovetail-shaped key 4' integral with a vertical leg of a slider of generally L-shaped profile. The slider also has a horizontal leg forming a shelf 5' which again overlies part of the trough at the level of the upper shell rim for releasably retaining a body of plaster of paris or the like molded within the trough.

It will be readily apparent that any segment of such a molded body, with vertical ribs complementary to the corrugations 3 or 3', can be positively located within the mold even if separated by small gaps from adjoining segments.

The mold shown in FIGS. 1– 6 may easily be designed in such a way that its trough accommodates the false roots of different dentures conforming to a wide variety of human jaws.

I claim:

1. A mold for the temporary retention of a plurality of false roots for a multitooth denture, comprising:
   a shell with a bottom, a central portion and a peripheral wall defining an upwardly open generally U-shaped trough of an outline conforming to a human jaw, said trough having a generally trapezoidal, upwardly diverging cross-section with bottom and side surfaces provided with closely spaced transverse corrugations facilitating the precise repositioning in said trough of a segment of a molded mass temporarily removed therefrom; and
   a slider of generally T-shaped profile removably seated in said shell, said slider having a shelf partly overhanging said trough for holding said mass in place while giving access to false roots embedded in said mass, said slider being provided with a key forming the web of the T, said key being received in a complementary horizontal keyway formed in said central portion.

2. A mold as defined in claim 1 wherein said shelf has the shape of a tongue with a tip pointing toward the bight of the U-shaped trough.

3. A mold as defined in claim 1 wherein said shell has an underside provided with at least one dovetail-shaped rail receivable in a layer of hardenable material on an articulator.

4. A mold as defined in claim 3 wherein said rail converges toward one end thereof.

5. A mold as defined in claim 3 wherein said rail consists at least on its surface of a substance nonadhering to plaster of paris.

6. A mold as defined in claim 5 wherein said substance is polyethylene or polytetrafluoroethylene.

7. A mold as defined in claim 1 wherein said shell is provided at the bottom of said trough with air holes for aiding in the dislodgement of said molded mass.

8. A mold as defined in claim 1 wherein said key and said keyway are dovetail-shaped.

9. A mold for the temporary retention of a plurality of false roots for a multitooth denture, comprising:
   a shell with a bottom and sidewalls defining an upwardly open trough of an outline conforming to part of a human jaw, said trough having a generally trapezoidal, upwardly diverging cross-section with bottom and side surfaces provided with closely spaced transverse corrugations facilitating the precise repositioning in said trough of a segment of a molded mass temporarily removed therefrom; and
   a slider of generally L shaped profile removably seated on said shell, said slider being provided with a horizontal leg forming a shelf partly overhanging said trough for holding said mass in place while giving access to false roots embedded in said mass, said slider being further provided with a dovetail-shaped key on a vertical leg thereof received in a complementary horizontal keyway in an outer surface of one of said sidewalls.

* * * * *